(12) United States Patent
Bailey et al.

(10) Patent No.: US 12,588,845 B2
(45) Date of Patent: *Mar. 31, 2026

(54) LIQUID COLLECTION DEVICE

(71) Applicant: University of Tasmania, Sandy Bay (AU)

(72) Inventors: David Charles Bailey, Ringwood (AU); Andrew Gooley, Ringwood (AU); Florian Germain Lapierre, Sandy Bay (AU); David John Melville, Ringwood (AU); Rod Anthony Wiebenga, Cremorne (AU); Chau Hoang Thanh Nguyen, Cremorne (AU); Eugen Meyer, Cremorne (AU)

(73) Assignee: University of Tasmania, Sandy Bay (AU)

( * ) Notice: Subject to any disclaimer, the term of this patent is extended or adjusted under 35 U.S.C. 154(b) by 1004 days.

This patent is subject to a terminal disclaimer.

(21) Appl. No.: 17/586,961

(22) Filed: Jan. 28, 2022

(65) Prior Publication Data

US 2022/0160272 A1 May 26, 2022

Related U.S. Application Data

(63) Continuation of application No. 15/751,664, filed as application No. PCT/AU2016/050749 on Aug. 12, 2016, now Pat. No. 11,278,225.

(30) Foreign Application Priority Data

Aug. 12, 2015 (AU) ................................. 2015903220

(51) Int. Cl.
*A61B 5/15* (2006.01)
*A61B 5/151* (2006.01)
(Continued)

(52) U.S. Cl.
CPC .. *A61B 5/150343* (2013.01); *A61B 5/150022* (2013.01); *A61B 5/150236* (2013.01);
(Continued)

(58) Field of Classification Search
CPC ........ A61B 5/150343; A61B 5/150022; A61B 10/0045; A61B 5/150755; A61B 5/15144;
(Continued)

(56) References Cited

U.S. PATENT DOCUMENTS 3,898,982 A 8/1975 Katsuda
4,360,016 A 11/1982 Sarrine
(Continued)

FOREIGN PATENT DOCUMENTS

AU 2005216692 A1 * 9/2005 ............. A61B 10/02
CA 2653631 A1 * 12/2007 ....... A61B 5/150717
(Continued)

OTHER PUBLICATIONS

Gong, M. et al., "Lab-in-a-pen: a diagnostics format familiar to patients for low-resource settings", Lab Chip, 14: 957-963 (2014).
(Continued)

*Primary Examiner* — Sean P Dougherty
(74) *Attorney, Agent, or Firm* — Merchant & Gould P.C.

(57) ABSTRACT

A pen format liquid collection device includes an elongate generally tubular housing (12, 112, 212, 312) able to be held by hand and having an opening at one end, and at least one liquid take-up element (30, 130, 230, 330) mounted in the housing so as to be positioned or positionable to project at the opening, the at least one liquid take-up element then further postionable by hand manipulation of the housing to contact a volume of liquid to thereby take-up a sample of the liquid to be analysed. At least one retention element (230a, 330a) is supported in the housing. The at least one liquid take-up element and the at least one retention element are
(Continued)

A arranged whereby they are relatively movable into contact, and the at least one retention element is adapted on contact to in turn take-up the sample and retain the sample or a component thereof for in situ analysis or later recovery while protected within the housing. The liquid take-up element is preferably a capillary.

41 Claims, 11 Drawing Sheets

(51) Int. Cl.
    *A61B 10/00*       (2006.01)
    *G01N 1/02*        (2006.01)

(52) U.S. Cl.
    CPC .. *A61B 5/150358* (2013.01); *A61B 5/150755* (2013.01); *A61B 5/15144* (2013.01); *A61B 10/0045* (2013.01); *G01N 1/02* (2013.01); *A61B 5/150183* (2013.01); *A61B 5/150305* (2013.01); *A61B 5/150412* (2013.01); *A61B 5/150503* (2013.01); *A61B 5/151* (2013.01); *A61B 5/15113* (2013.01); *A61B 2010/008* (2013.01); *G01N 2001/028* (2013.01)

(58) Field of Classification Search
    CPC .............. A61B 5/151; A61B 5/150412; A61B 5/15113; A61B 5/150503
    See application file for complete search history.

(56) References Cited

U.S. PATENT DOCUMENTS

| | | | |
|---|---|---|---|
| 4,580,918 A | 4/1986 | Baker et al. | |
| 4,589,421 A | 5/1986 | Ullman | |
| 4,635,488 A | 1/1987 | Kremer | |
| 5,100,620 A | 3/1992 | Brenneman | |
| 5,602,040 A | 2/1997 | May et al. | |
| 5,833,630 A | 11/1998 | Kloth | |
| 6,099,484 A | 8/2000 | Douglas et al. | |
| 6,319,209 B1 * | 11/2001 | Kriz ................. | A61B 5/150412 |
| | | | 600/583 |
| 6,591,125 B1 | 7/2003 | Buse et al. | |
| 7,378,054 B2 * | 5/2008 | Karmali ........... | A61B 5/150022 |
| | | | 422/410 |
| 7,828,749 B2 * | 11/2010 | Douglas ........... | A61B 5/150236 |
| | | | 600/583 |
| 8,852,122 B2 | 10/2014 | Mao et al. | |
| 9,795,660 B2 | 10/2017 | Sandler et al. | |
| 10,371,606 B2 | 8/2019 | Holmes et al. | |
| 10,823,745 B2 | 11/2020 | Yamashita et al. | |
| 10,856,791 B2 | 12/2020 | McHale et al. | |
| 10,973,497 B2 | 4/2021 | Sessions et al. | |
| 2002/0002344 A1 | 1/2002 | Douglas et al. | |
| 2005/0232813 A1 * | 10/2005 | Karmali ........... | A61B 5/150022 |
| | | | 422/410 |
| 2006/0008389 A1 | 1/2006 | Sacherer et al. | |
| 2007/0093728 A1 | 4/2007 | Douglas et al. | |
| 2008/0025872 A1 | 1/2008 | Dykes et al. | |
| 2009/0149725 A1 | 6/2009 | Gofman et al. | |
| 2009/0259145 A1 | 10/2009 | Bartfeld et al. | |
| 2011/0004122 A1 | 1/2011 | Sangha | |
| 2011/0020195 A1 | 1/2011 | Luotola | |
| 2012/0101407 A1 | 4/2012 | Chan | |
| 2013/0116597 A1 | 5/2013 | Rudge et al. | |
| 2014/0073990 A1 | 3/2014 | Holmes et al. | |
| 2014/0127669 A1 | 5/2014 | Hilder et al. | |
| 2014/0248197 A1 | 9/2014 | Hur | |
| 2014/0249451 A1 | 9/2014 | Mao et al. | |
| 2014/0316300 A1 | 10/2014 | Holmes et al. | |
| 2014/0323911 A1 | 10/2014 | Sloan et al. | |
| 2014/0323913 A1 | 10/2014 | Holmes et al. | |
| 2014/0342371 A1 | 11/2014 | Holmes | |
| 2014/0358036 A1 | 12/2014 | Holmes | |
| 2015/0211967 A1 | 7/2015 | Gooley et al. | |
| 2015/0231627 A1 | 8/2015 | Sloan et al. | |
| 2016/0045148 A1 | 2/2016 | Al-Uzri et al. | |
| 2018/0235528 A1 | 8/2018 | Bailey et al. | |

FOREIGN PATENT DOCUMENTS

| | | | | |
|---|---|---|---|---|
| CA | 2833175 A1 | 11/2012 | | |
| CN | 201510290 U | 6/2010 | | |
| CN | 101637390 B | 9/2011 | | |
| CN | 103874461 A | 6/2014 | | |
| JP | 2002503118 A | * 1/2002 | ......... | A61B 5/14532 |
| WO | 2010002072 A1 | 1/2010 | | |
| WO | 2013067760 A1 | 5/2013 | | |

OTHER PUBLICATIONS

International Search Report and Written Opinion of the International Searching Authority for corresponding International Patent Application No. PCT/AU2016/050749 mailed Nov. 22, 2016, 11 pages.

* cited by examiner

LIQUID COLLECTION DEVICE

CROSS-REFERENCE TO RELATED APPLICATIONS

This application is a continuation of U.S. application Ser. No. 15/751,664, filed 9 Feb. 2018, now U.S. Pat. No. 11,278,225, which is a U.S. National Stage Application of PCT/AU2016/050749, filed 12 Aug. 2016, which claims benefit of Serial No. 2015903220, filed 12 Aug. 2015 in Australia, and which applications are incorporated herein by reference. To the extent appropriate, a claim of priority is made to each of the above disclosed applications.

FIELD OF THE INVENTION

This invention relates generally to the collection of liquid samples for analysis and more particularly to microfluidic devices for collecting blood or other fluid samples from patients for simultaneous or subsequent diagnosis. In one or more embodiments, the invention provides a pen format liquid collection device that has application to the collection of blood micro samples from pin prick blood spots.

BACKGROUND TO THE INVENTION

The conventional method of obtaining diagnostic blood samples from patients necessarily involves a medical professional who either employs a hypodermic syringe or fits a temporary cannula to the patient's arm and draws off a succession of discrete samples into separate vials, each typically dedicated to one or more specific analyses. With a trend to smaller sample volumes, a number of microfluidic point of care diagnostic devices have been developed for a range of analytic purposes. Most such devices are relatively costly and complex to operate and, while avoiding the need to transport blood samples for analysis in laboratory settings, still require operation by skilled medical staff. It would be advantageous to the delivery of healthcare if microfluidic blood samples could be collected by relatively untrained personnel or even by patients themselves. Devices for self-testing of blood sugar level and home pregnancy kits are examples of successful products in which untrained individuals can perform diagnostic tests on themselves, in one case utilising finger prick blood spots and in the other urine collection.

In a paper entitled 'Lab-in-a-pen: a diagnostics format familiar to patients for low-resource settings' at *Lab Chip* 2014, 14, 957, Gong et al describe a pen format device that incorporates a finger actuable lancet and a paper assay with a collection pad adjacent the lancet blade. Prior to and after deployment, an end cap covers the exposed lancet blade and collection pad.

U.S. Pat. No. 4,360,016 discloses a not dissimilar pen format blood collection device for the specialised purpose of foetal blood sampling. The finger actuable lancet pierces the skin on the head of the foetus and blood is collected in an adjacent capillary tube. This tube is detachably mounted by clips at a fixed position, that places an open end of the tube below the lancet blade when deployed.

It is an object of the invention to provide a pen format liquid collection device that provides one or more advantages relative to the aforedescribed devices.

Reference to any prior art in the specification is not an acknowledgment or suggestion that this prior art forms part of the common general knowledge in any jurisdiction or that this prior art could reasonably be expected to be combined with other pieces of prior art by a skilled person in the art.

SUMMARY OF THE INVENTION

It has been appreciated that prior proposed devices such as those discussed above have significant limitations, most notably exposure of the blood collection element to potential contamination. There is also a potential for needle stick injuries from the lancet components of the devices.

In a first aspect, the invention provides a pen format liquid collection device that includes an elongate generally tubular housing able to be held by hand and having an opening at one end, and at least one liquid take-up element mounted in the housing so as to be positioned or positionable to project at the opening, the at least one liquid take-up element then further postionable by hand manipulation of the housing to contact a volume of liquid to thereby take-up a sample of the liquid to be analysed. At least one retention element is supported in the housing. The at least one liquid take-up element and the at least one retention element are arranged whereby they are relatively movable into contact, and the at least one retention element is adapted on contact to in turn take-up the sample and retain the sample or a component thereof for in situ analysis or later recovery while protected within the housing.

In an embodiment, the at least one retention element is supported in a carrier that is mounted in the housing for sliding movement to bring the at least one retention element into contact with the at least one liquid take-up element. The carrier may be a cartridge recoverable from the housing for subsequent analysis of the sample or component thereof.

The device may further include a detachable cover about the projecting portion of the at least are liquid take-up element. This cover may also provide a base for supporting the device upright on a surface.

In an embodiment, the cover includes interengagable formations for locking the cover to the housing after a sample has been taken-up to prevent re-use of the device.

Preferably, the at least one liquid take-up element and the at least one retention element are arranged whereby they are relatively movable into contact by hand action.

In an embodiment liquid take-up element is mounted for respective first and second movements, wherein the first movement is from a first retracted condition within the housing to an extended condition at the opening in which the liquid take-up element is postionable, by hand manipulation of the housing, to contact a volume of liquid to thereby take-up a sample of the liquid to be analysed, and wherein the second movement is from the extended condition to a second retracted condition within the housing in contact with the at least one retention element. The respective first and second retracted conditions may be co-incident.

In an embodiment, the at least one liquid take-up element may be an absorbent body of material selected to absorb a sample of the liquid on contact with the volume of liquid.

In another embodiment, the at least one liquid take-up element is a capillary open at a first or distal end that in operation contacts said volume of liquid and at a second or proximate end that in operation contacts the at least one retention element.

The at least one retention element is preferably an absorbent body selected to absorb the whole of the sample from the at least one liquid take-up element when the two contact.

The sample may be of a pre-determined or prescribed volume.

In an embodiment, there are plural said liquid take-up elements within the housing, for example three or more equi-angularly arranged about the housing. Plural said retention elements may be contactable with the respective liquid take-up elements.

In a second aspect, the invention provides a pen format liquid collection device, that includes an elongate generally tubular housing able to be held by hand and having an opening at one end, and a plurality of capillary liquid take-up elements in the housing postionable, by hand manipulation of the housing, to contact a volume of liquid to thereby take-up a predetermined total volume of a sample of the liquid to be analysed, wherein the capillary liquid take-up elements are configured to take-up by capillary action respective predetermined volume portions of the sample and notwithstanding gravity to retain the portions in any orientation of the respective elements. At least one retention element is supported in the housing positionable to contact the capillary take-up elements and adapted on contact to in turn take-up the sample and retained the sample or a component thereof for in situ analysis or later recovery while protected within the housing.

The at least one retention element may be supported in a carrier that is mounted in the housing for sliding movement to bring the at least one retention element into contact with the plurality of capillary liquid take-up elements. The carrier may be a cartridge recoverable from the housing for subsequent analysis of the sample or component thereof.

Each capillary liquid take-up element is preferably open at a first or distal end that in operation contacts said volume of liquid and at a second or proximate end that in operation contacts the at least one retention element.

In another aspect of the invention, the capillary liquid take-up elements may each have a liquid collection volume in the range 1 to 10 µL, for example in the range 2 to 5 µL.

In a third aspect, the invention provides a pen format liquid collection device, comprising:

an elongate generally tubular housing able to be held by hand and having an opening at one end;

a liquid take-up element mounted for respective first and second movements, wherein the first movement is from a first retracted condition within the housing to an extended condition at said opening in which the liquid take-up element is positionable, by hand manipulation of the housing, to contact a volume of liquid to thereby take up a sample of the liquid to be analysed, and wherein said second movement is from the extended condition to a second retracted condition within said housing in which the sample taken up is retained for in situ analysis or later recovery while protected within the housing from contamination; and a hand operable actuator for effecting said first and second movements.

In an embodiment, the liquid take-up element is an absorbent body of material selected to absorb a sample, preferably a prescribed volume thereof, of the liquid on contract with said volume of liquid. In an alternative embodiment, preferred for applications such as blood collection, the liquid take-up element is a capillary tube open at a distal end that contacts said volume of liquid in its extended condition and is arranged to contact a respective absorbent body in its second retracted condition, the absorbent body being selected to absorb the whole of the sample from the capillary tube when the tube is in the second retracted condition. With this arrangement, a pre-determined sample volume is taken up, determined by the retention volume of the capillary tube.

The respective first and second retracted conditions are preferably co-incident.

Preferably, there are plural liquid take-up elements within said housing, for example three or more equi-angularly arranged about the housing. There may be separate actuators for each element or a single actuator mechanism with respective selectable settings corresponding to each element.

In an advantageous embodiment of the invention, in any of its aspects, the pen format liquid collection device further includes a lancet mechanism including a blade projectable from the opening at said one end of the housing. A device thus configured may be employed to effect a finger prick and immediately collect a plurality of blood samples corresponding to the number of liquid take-up elements provided in the housing, or alternatively be employed to collect separate blood samples from different locations or at different times.

Advantageously, the device is configured so that the blood sample(s) can only be recovered by a designated person employing a designated tool. Preferably, in the device containing plural liquid take-up capillary tubes, the absorbent bodies are contained within a discrete sub-housing from which they are removable for recovery of the samples and analysis thereof. For this purpose, the housing is in plural separate parts and slidably receives the absorbent body sub-housing.

The invention also extends to any combination of the first, second and third aspects, or of their optimal and preferred features.

As used herein, except where the context requires otherwise the term 'comprise' and variations of the term, such as 'comprising', 'comprises' and 'comprised', are not intended to exclude other additives, components, integers or steps.

BRIEF DESCRIPTION OF THE DRAWINGS

The invention will now be further described, by way of example only, with reference to the accompanying drawings, in which.

5

Figure 8:
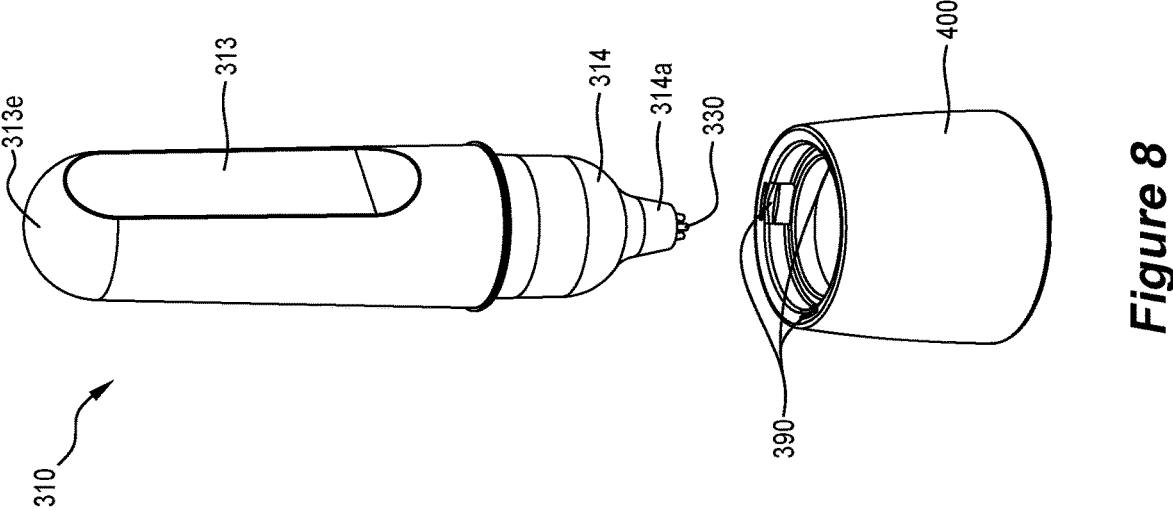
FIG. 8 shows the embodiment of FIG. 7 and its mode of engagement with the dual purpose cover and support base.
Figure 7:
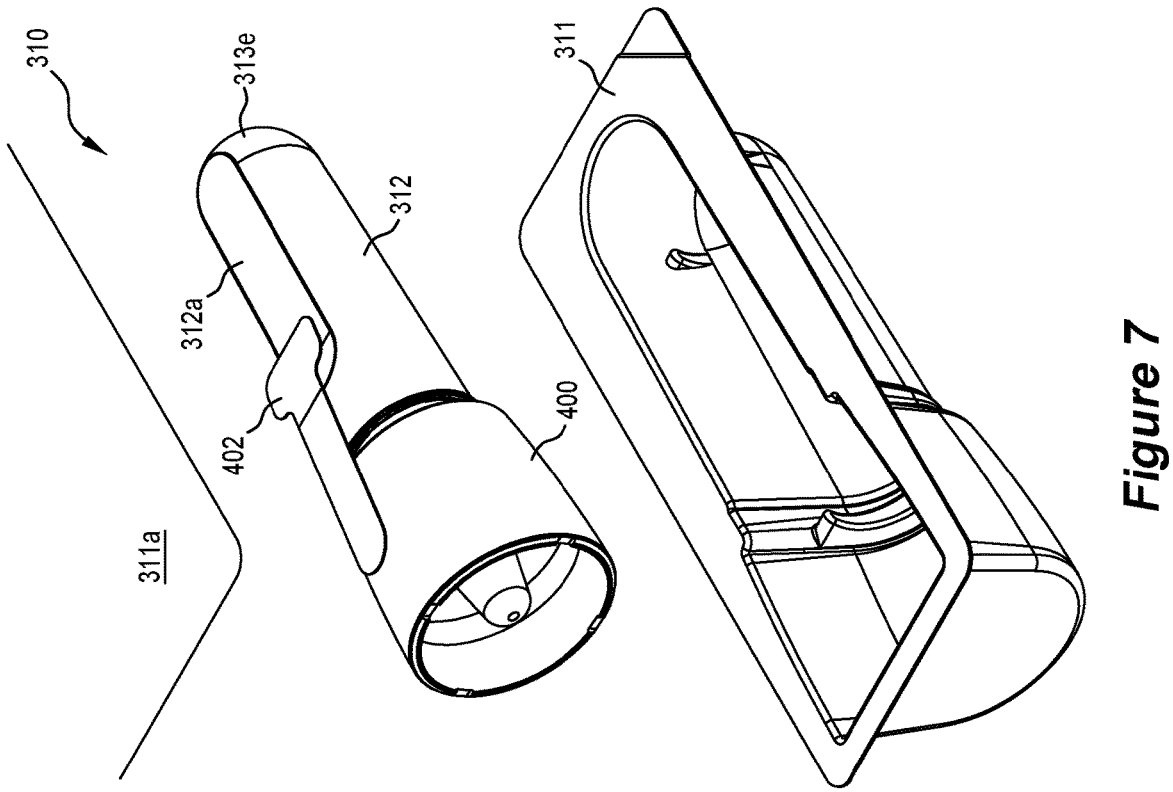
FIG. 7 is a perspective view of a pen format blood collection device according to a fourth embodiment of the invention, together with a dual purpose cover and support base and an associated package for delivery of the device to a point of use and return for analysis of one or more contained blood samples.
Figure 9:
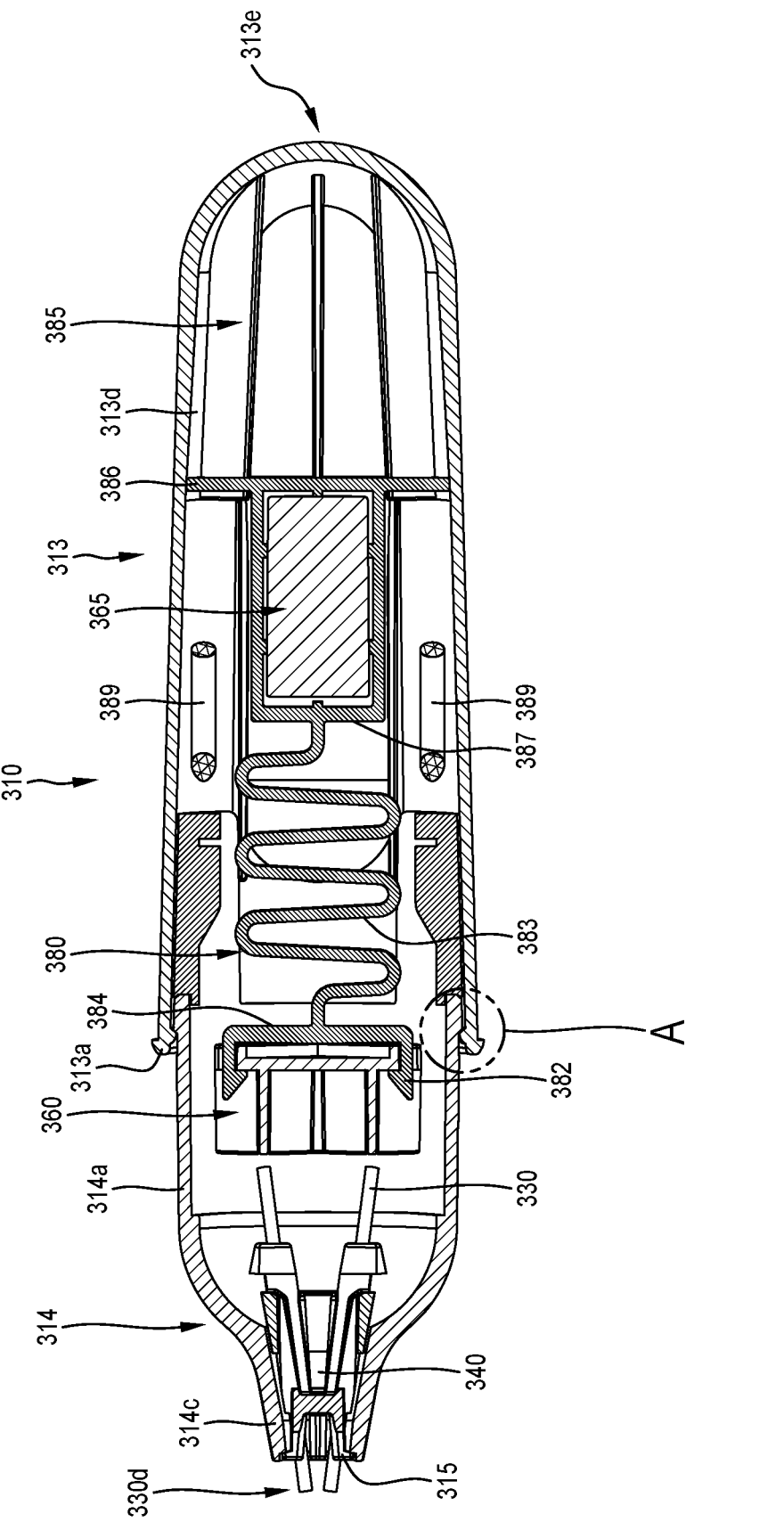
Figure 11:
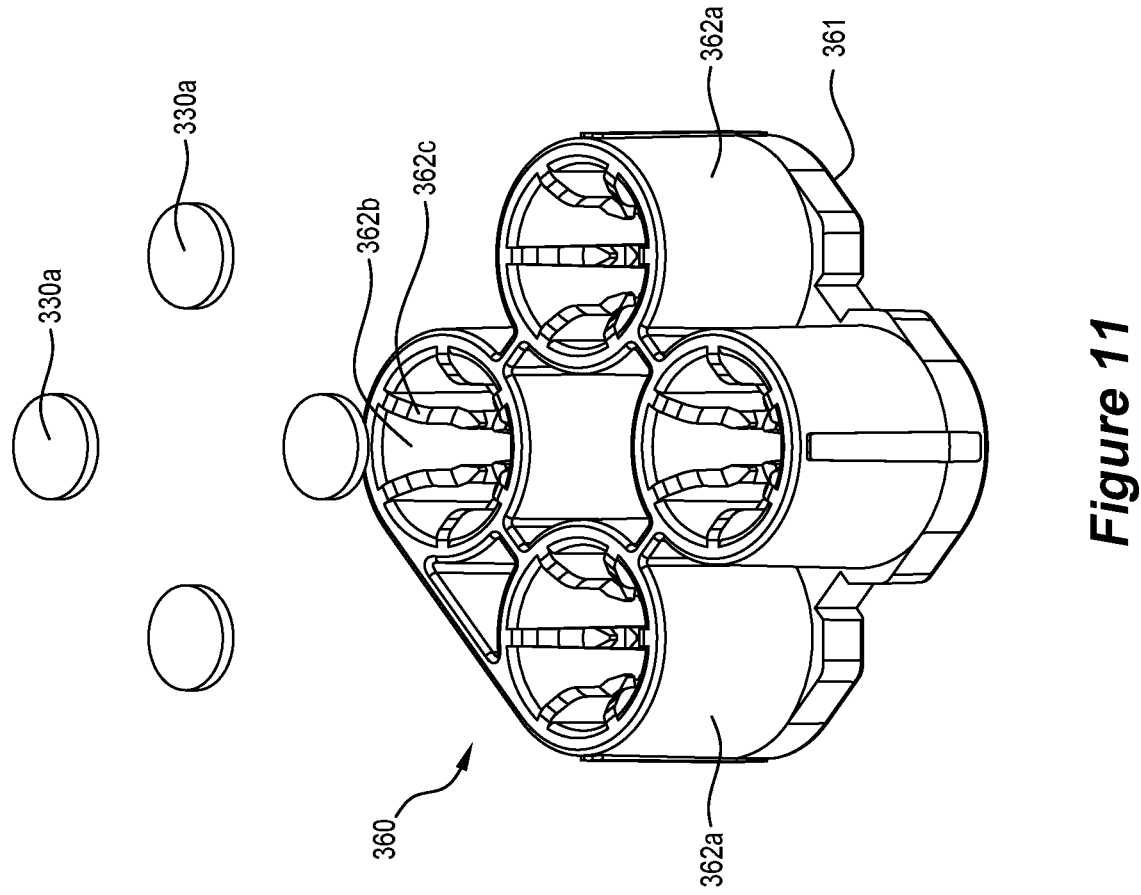
Figure 10:
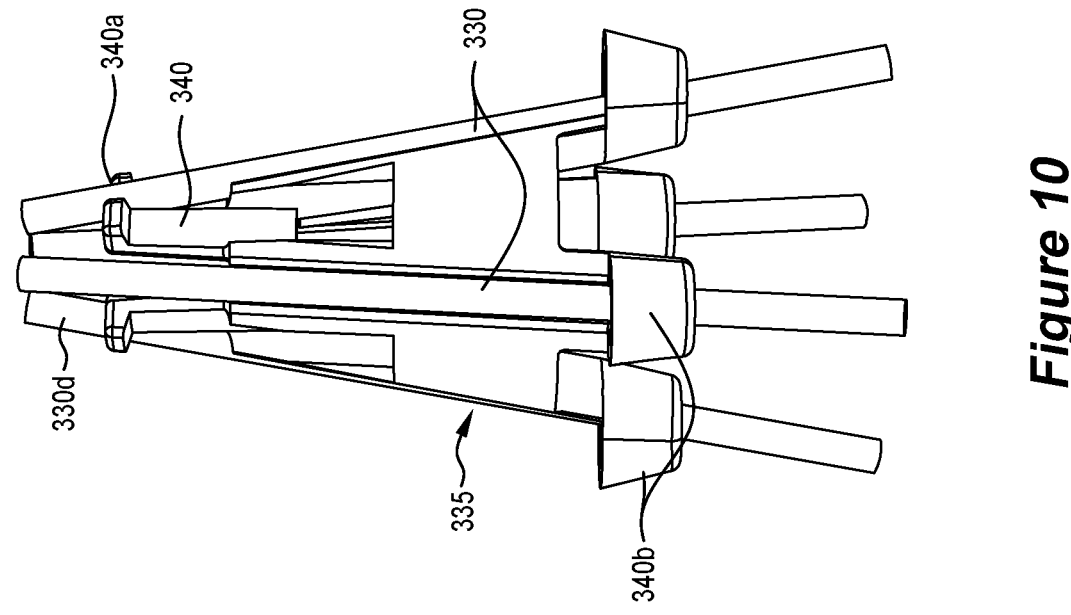
Figure 13:
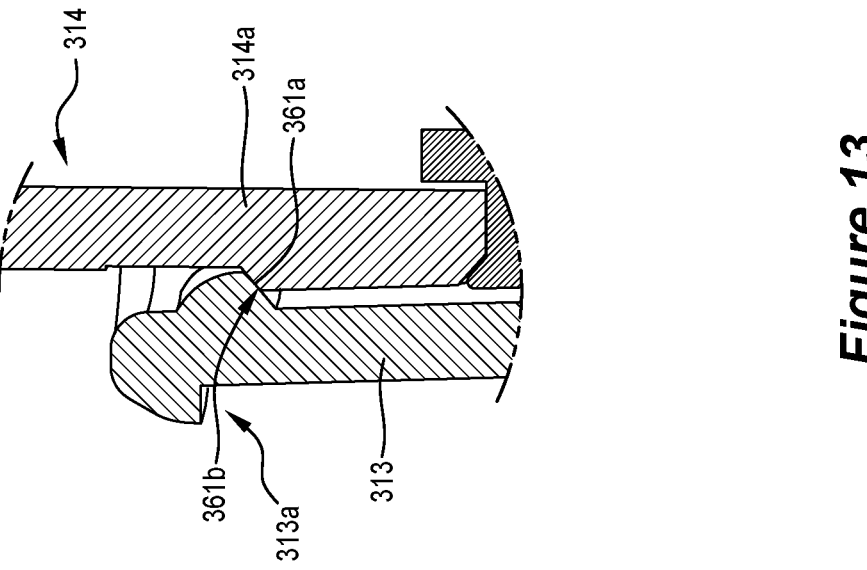
Figure 12:
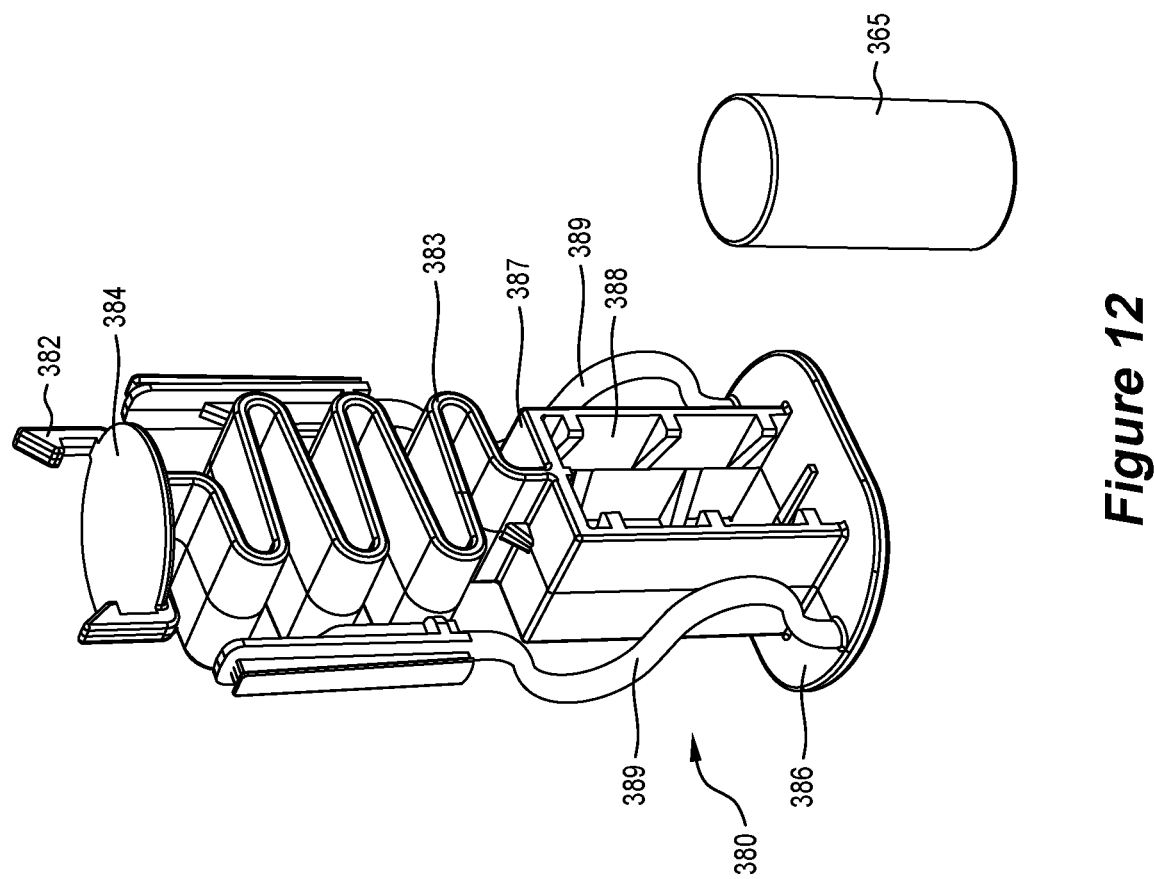

FIG. 9 is an axial cross-section of the device of FIGS. 7 and 8;

FIGS. 10, 11 and 12 are respective 3-dimensional component views of the capillary tube sub-assembly, the cartridge containing the absorbent pads, and the integral spring structure; and FIG. 13 is a fragmentary englargement of region A in FIG. 9.

DETAIL DESCRIPTION OF EMBODIMENTS

Figure 1C:
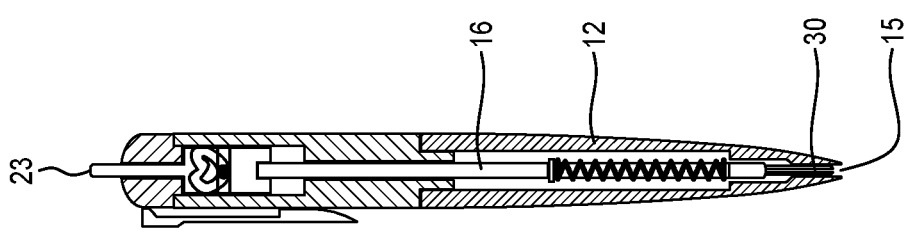
FIGS. 1A-1C are an axial cross sectional view of a pen format blood collection device according to a first embodiment of the invention, depicted before, during and after deployment to recover a blood sample from a pin prick volume of blood.
Figure 1B:
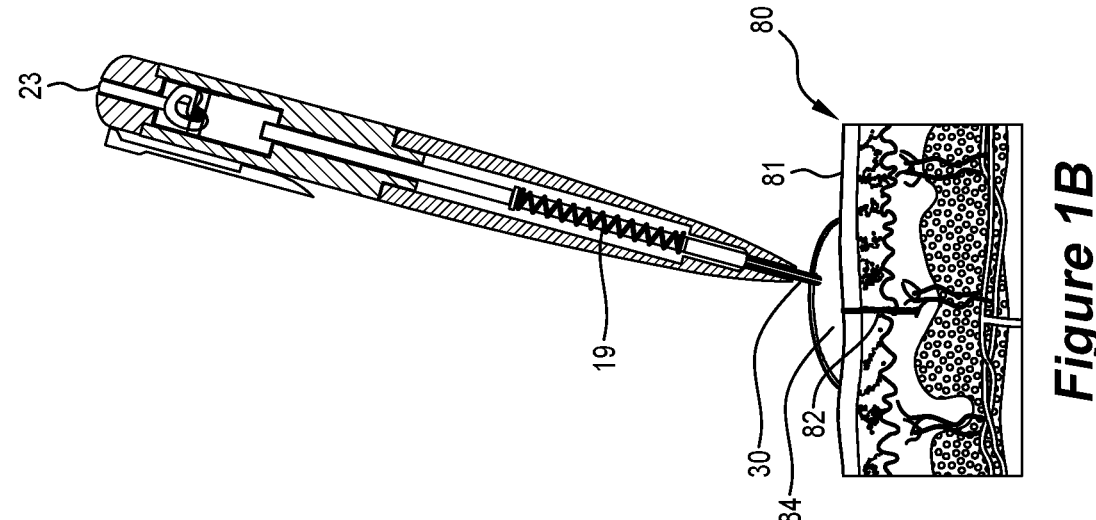
Figure 1A:
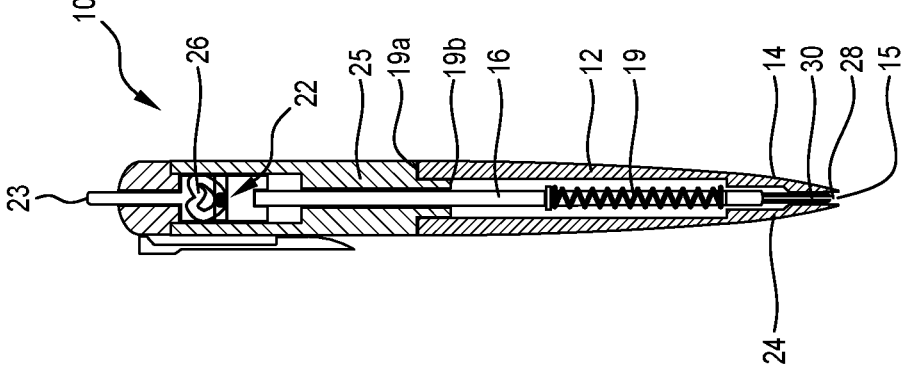

The pen format blood collection device 10 illustrated in FIG. 1 is designed to recover and retain a single blood sample of a predetermined micro volume, for example in the range 5 to 30 μl. A volume of 15 μl, e.g, is commonly accepted as necessary but sufficient for dry blood spot analysis. The embodiment is essentially a ballpoint pen modified by replacing the ink ball with a liquid take-up element in the form of a liquid take-up element comprising a cylindrical body of absorbent material selected, both as to substance and dimensions, to absorb 15 μl of blood. A suitable such material is a porous polymer substrate, a hydrophilic cellulose paper, a monolith polymer, or any equivalently performing inert porous material.

Other than absorbent liquid take-up element 30, the device 10 includes the usual features of a pen mechanism, including a generally tubular housing or barrel 12 that is of substantially uniform diameter at its rear end and gently tapers at its front end to a conical tip 14 with a central end opening 15. The mechanism includes a coaxial plunger 16 (which in a pen also serves as the ink-containing tube), a return spring 19 under compression between respective shoulders 19a and 19b on housing 12 and plunger 16, and a push button mechanism 22. Mechanism 22 has an internal cam device 26 whereby, when push stem 23 is depressed by finger or thumb, the plunger 16 is pushed to and held in an extended position and when push stem 23 is again depressed this position is unlatched and spring 19 pushes the plunger back to its retracted position.

The forward end of plunger 16 is sealed off and fitted with a liquid absorbent to form liquid take-up element 30, which is slidably smoothly guided by a bore 28 of complementary radius extending back from opening 15. In the retracted position of plunger 16 and therefore of liquid take up element 30, the liquid take-up element is disposed as illustrated in FIG. 1(*a*): it is protected from contamination prior to use by having its front tip recessed along bore 28 behind opening 15.

When it is time to collect the blood sample from a finger or thumb 80 or any other suitable location on the skin surface of an individual, a suitable lancet (not shown) is employed to puncture the skin to form a pin prick 82 from which a small volume of blood 84 pools on the skin 81 (FIG. 1(*b*)). Collection device 10 is prepared to recover a blood sample by depressing push stem 23 to move liquid take-up element 30 forwardly so that it reaches its extended condition at and protruding from opening 15. The housing of device 10 is now manipulated to bring element 15 into contact with the volume of pooled blood 84 whereupon the absorbent material of element takes up therefrom a sample of the blood (FIG. 1(*b*)). After an appropriate time, the device is withdrawn and push stem 23 is pushed to retract liquid take up element 30 and its entrained blood sample into housing 12 behind opening 15. In this retracted condition (FIG. 1(*c*)), element 30 now serves as a retention or absorbent element retaining the taken up blood sample for later recovery and analysis while in the meantime protected from contamination.

The embodiment of FIG. 1 is satisfactory for more qualitative applications, e.g. analysis as to whether a blood sample does or does not contain a particular virus or other marker. For more quantitative analyses, e.g. detection of protein markers such as haemoglobin A1c (HbA1c), where a known volume of blood is required, the application of the embodiment of FIG. 1 will be reliant upon the take-up or absorbent element 30 consistently taking up a prescribed volume of blood. While certain manufacturers claim that this is so, it is found in practice that the actual volume taken up by liquid absorbent material is dependent upon the haematocrit of the blood, which varies considerably between individuals within a wide normal range. The embodiment 110 of FIGS. 2 to 4 addresses this uncertainty by providing the take-up element as a glass capillary tube and providing an absorbent retention element as a separate component. This embodiment also demonstrates a more complex device capable of recovering and retaining four discrete samples.

Figure 2:
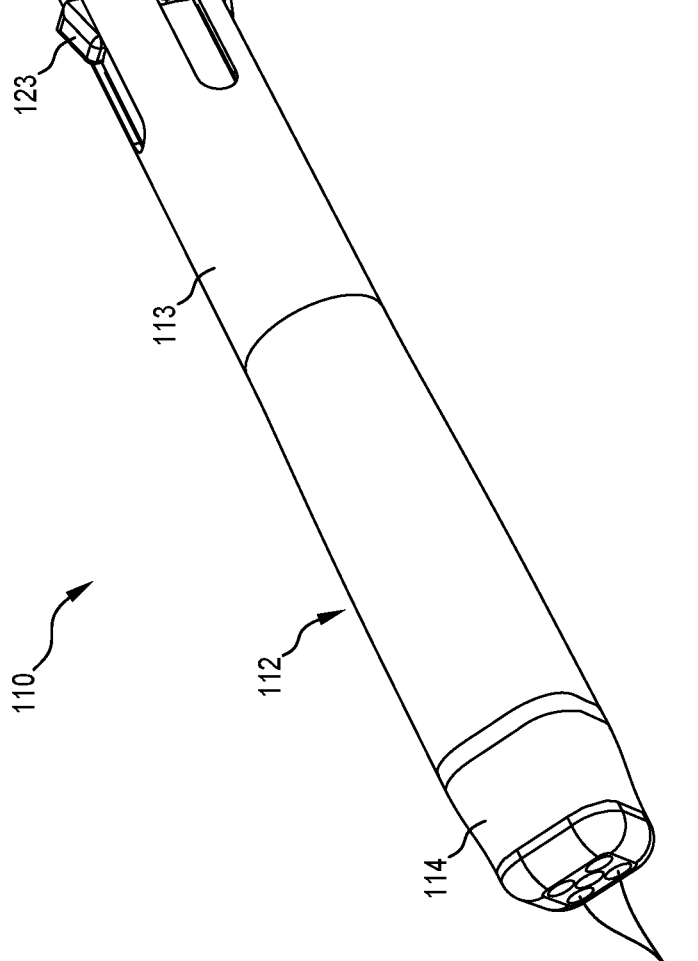
FIG. 2 is a perspective view of a pen format blood collection device according to a second embodiment of the invention, capable of recovering and retaining four discrete blood samples.
Figure 3A:
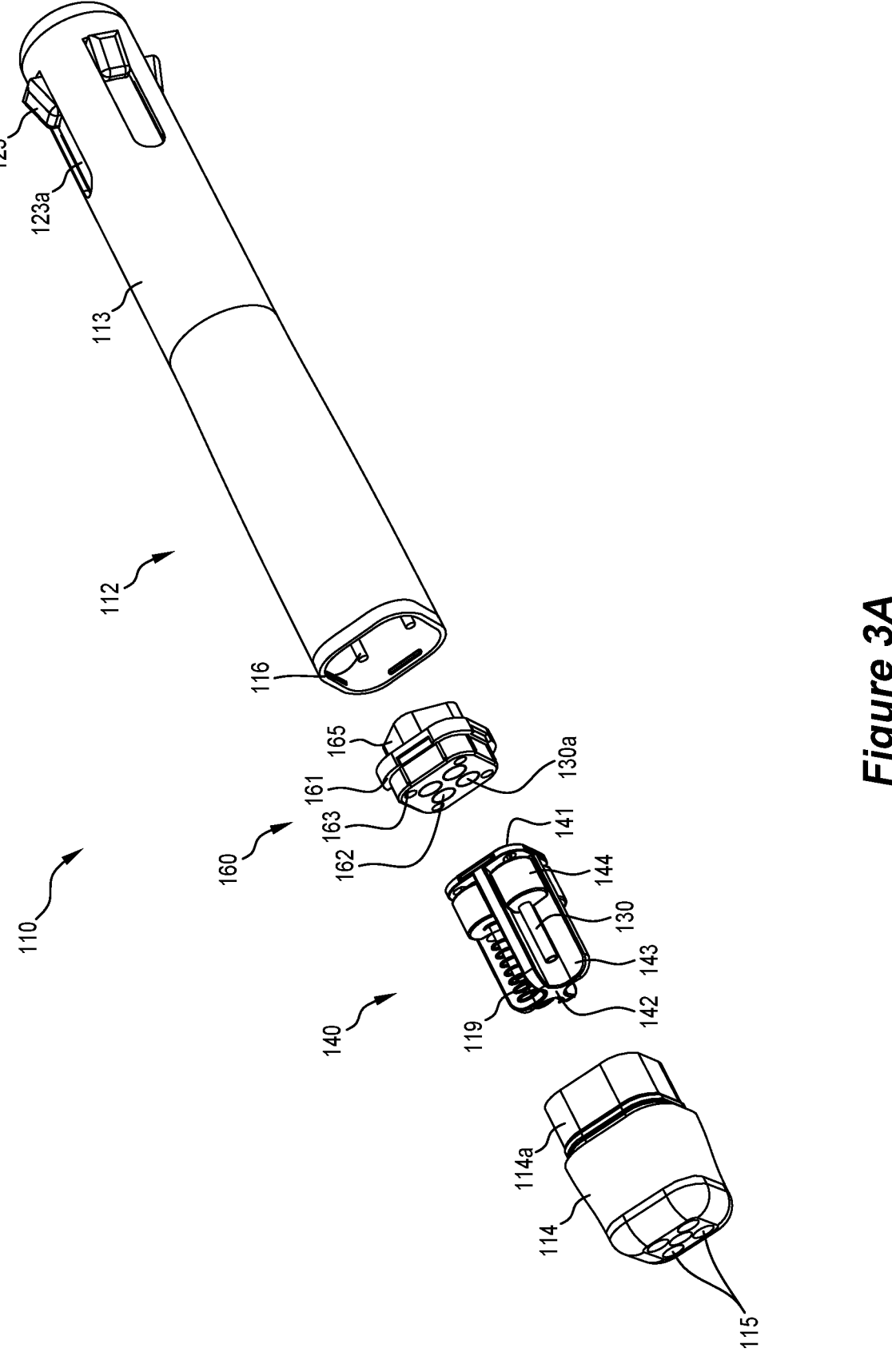
FIGS. 3A and 3B are a pair of exploded views of the device illustrated in FIG. 2.
Figure 3B:

Continuing the pen format, the four sample device 110 of FIGS. 2-4 has a structure inspired by a 4 colour ballpoint pen. In FIGS. 2-4, corresponding elements relative to the embodiment of FIG. 1 are depicted with similar reference numerals preceded by a "1".

Device 110 includes a generally tubular housing or barrel 112 of "rounded square" cross section with a main section 113 and a separate nozzle cap 114. Nozzle cap 114 has a slight taper and a rearward skirt 114a by which it fits into the end of the main section 113 of housing 112. Nozzle cap 114, which is somewhat more blunt nosed than the tip 14 of housing 112 retains within it a glass capillary mount 140 and a blotting paper support 160. The whole structure has a 4-way angular symmetry with an identical discrete mechanism for each quarter to recover and retain a discrete blood sample.

To this end, glass capillary mount 140 is a moulded unitary piece with a base wall 141 and a cross-shaped partition structure 142 that defines four longitudinally extending compartments 143. Each compartment 143 slidably mounts a sector block 144 with an inner and outer bore. The inner bore receives and is fixed to an open-ended liquid take-up element in the form of a glass capillary tube 130 of an internal volume equal to the desired volume of blood, e.g. 15 μl. This glass capillary tube 130 projects slightly rearwardly from end wall 141.

The outer bore in sector block 144 is a blind bore at its rear, located axially outwardly of glass capillary tube 130. This blind bore receives and is fixed to the forward end of a plunger 116 that is slidable to move sector block 144 and therefore glass capillary tube 130 forwardly and rearwardly in chamber 143.

Blotting paper carrier or cartridge 160 is a rounded square integral plate with a peripheral rim 161 at its rear against which abuts the skirt 114a of nozzle cap 114. Blotting paper carrier 160 has four equiangular spaced inner bores 162 that mount cylindrical retention elements, ie. absorbent bodies 130a, and are aligned to be contacted by the rear open end of glass capillary tubes 130, when in their rearmost or retracted position. In this case, absorbent retention elements 130a are blotting papers selected to absorb and retain blood samples. Four outer bores 163 in carrier 160 slidably receive plungers 116.

The rear face of blotting paper carrier 160 mounts a hydrophilic silica gel capsule 165 for absorbing moisture from the blood samples on blotting paper absorbent retention elements 130a, for drying the blood samples while they are in situ within the device and readying them for dried blood spot analysis.

The respective plunger mechanisms for selectively moving the glass capillary tubes 130 are similar to those in a standard 4-colour ballpoint pen and include a retracting spring 119 about each glass capillary tube 130 and respective push clips 123 in side slots 123a of housing 112. Plungers 116 are located and guided by a central plunger guide 125 within the housing. The mechanism further includes a cam interaction 123b between the push clips 123 whereby depressing one will release and cause retraction of an already extended plunger under the action of its respective spring 119.

Figures 4A, 4B:
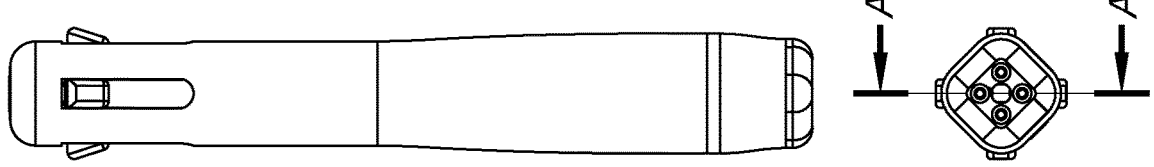
FIGS. 4A-4B are a fragmentary cross section of the device illustrated in FIGS. 2, 3A and 3B, depicted before and during deployment.

FIG. 4a illustrates the device of FIGS. 2 and 3 in a fully retracted condition ready for deployment. When it is desired to collect a blood sample, a selected clip 123 is depressed and pushed forwardly to push the corresponding plunger 116 and sector block 144 to move the associated glass capillary tube 130 against its spring 119 through a respective opening 115 in the blunt tip of nozzle cap 114. The glass capillary tube is now in its extended condition at opening 115 and is positionable by hand manipulation of housing 112 to contact a volume of blood obtained by a pin prick to take-up, through its open front end, a sample of the blood by capillary action. The sample fills the capillary tube and is of a fixed and predictable volume determined by the tube.

On depression of a different push clip 123, the projected plunger is released and the glass capillary tube retracted by its spring 119 from the extended condition to its retracted condition in which the open rear end of the glass capillary tube contacts respective blotting paper absorbent element 130a, which promptly takes up the entire blood sample and empties the glass capillary tube. The blood sample is thereby now retained within the housing for later recovery while protected in the meantime from contamination. Nozzle cap 114 is at least partly transparent to allow clear sighting of the filling and emptying of the capillary tube.

When the desired number of blood samples, at least one up to four in the embodiment as illustrated, have been collected, the device can be opened onsite by an authorised person or forwarded to another site for opening. Typically, this will require removal of nozzle cap 114 in a suitable environment, recovery of the blotting paper carrier 160 and extraction or punching out of the blotting paper absorption elements 130a by known means. The engagement of nozzle cap 114 to close the housing may desirably entail use of a specialised tool not readily available to the person originally collecting the blood.

Figure 5:
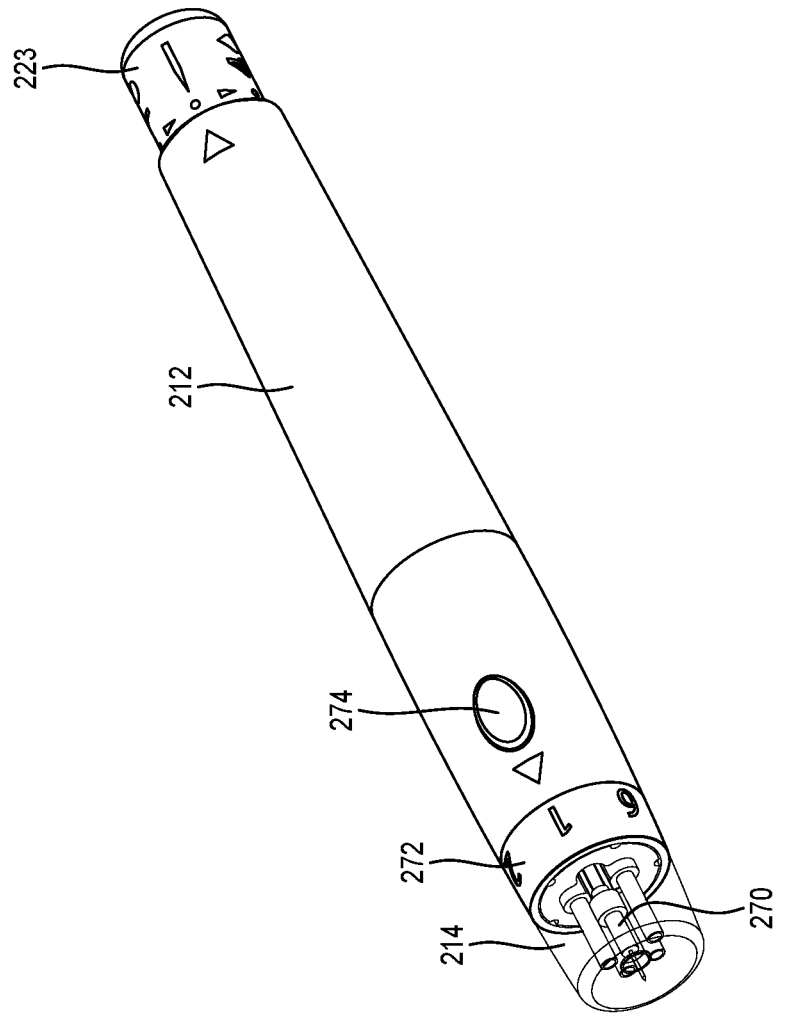
FIG. 5 is a perspective view of a pen format blood collection device according to a third embodiment of the invention incorporating a lancet for obtaining a pin prick volume of blood.
Figure 6:
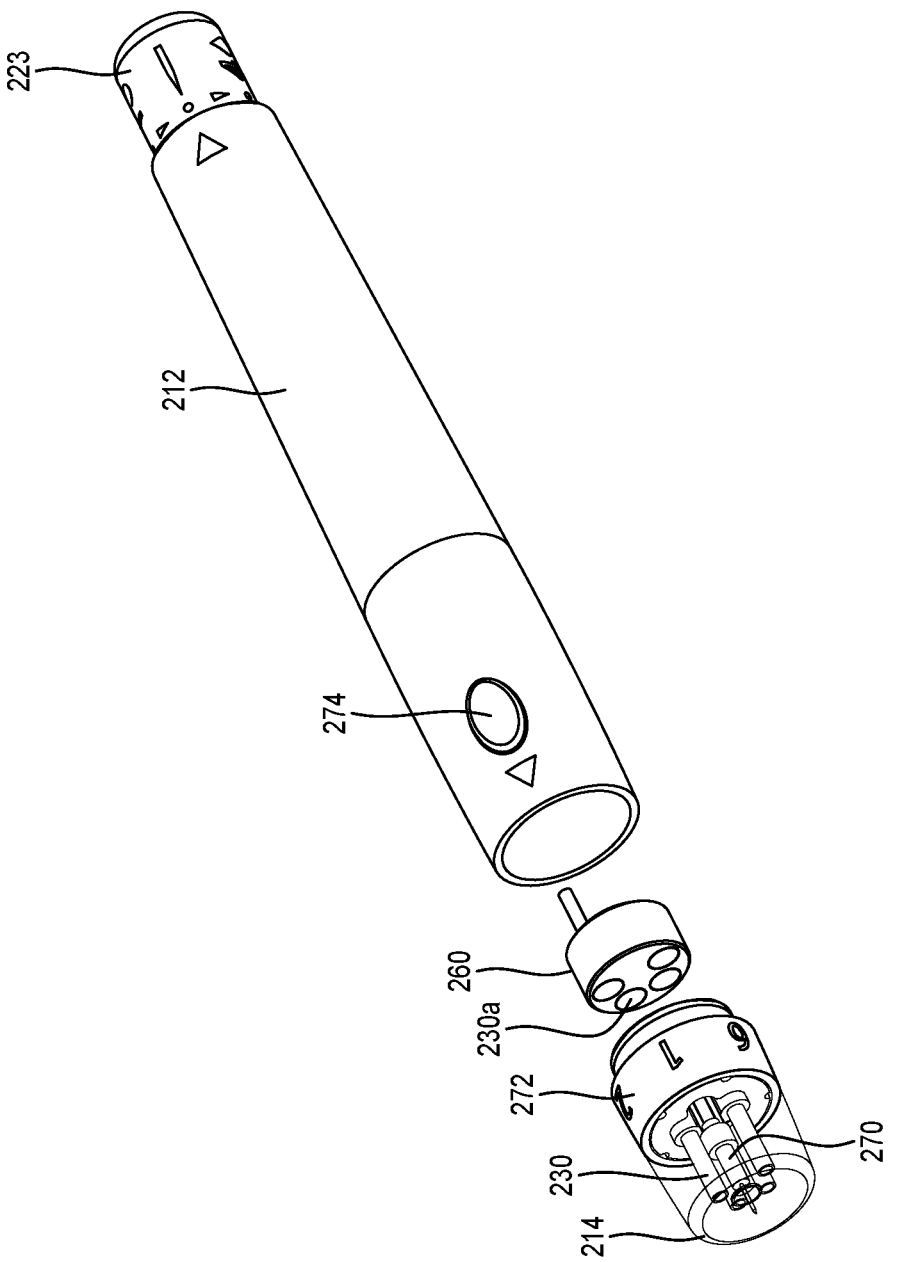
FIG. 6 is an exploded view of the device depicted in FIG. 5.

FIGS. 5 and 6 depict a third embodiment of pen format liquid collection device 210 which includes a central lancet device 270 for obtaining the pin prick blood volume to be taken up by the capillary tubes 230. In these figures, like parts relative to the first and second embodiments are indicated by like reference numerals preceded by a "2". The details of the mechanism are not fully illustrated but it is noted that this embodiment includes a rotatable lancet depth adjustment dial 272 and a lancet actuator button 274 on the side of the main housing 212. Rather than having separate push clips 123 as in the second embodiment, the rear of the housing is fitted with an actuator button 223 that is rotatable to select a glass capillary tube and then depressed to move the selected glass capillary tube 230 to its extended or deployed position for taking up blood from the volume extracted by the lancet device 270. As in the previous embodiment, the liquid absorbent retention elements are in the form of blotting paper elements 230a retained in a separate carrier component 260.

The device 10, 110 or 210 preferably includes a feature that prevents deployment of the liquid take-up element 30, 130, 230 more than once.

FIGS. 7 to 13 depict a fourth embodiment of pen format liquid collection device 310 which uses a single mechanism to transfer the contents of four blood capillaries simultaneously onto four independent absorbent pads. In this embodiment, like parts relative to the earlier illustrated embodiments are indicated by like reference numerals preceded by a "3". The pen 310 is positioned in a cover/base 400 in a disengaged position and is transported in a plastics package 311 that includes a sealing lid 311a—the pen and base are held in position together using an adhesive patch 402. Once the pen is removed from the package 311 it is placed on the base 400 in an upright position (FIG. 8).

This embodiment differs from the earlier embodiments in that a blotting paper carrier or cartridge 360 and the glass capillary tubes 330 are relatively movable to bring the absorbent retention elements 330a into contact with the inner ends of the glass capillary tubes 330, whereas in the earlier embodiments, the absorbent retention elements were fixed in position and the capillary tubes were longitudinally individually movable.

Device 310 includes a generally tubular housing or barrel 312 with opposed side flats 312a to facilitate manual gripping. The housing is in two parts: a main section 313 with a rounded closed rear end 313e and an open front rim 313a that receives a cylindrical skirt 314a of a front cap section 314. Engagement between respective peripheral shoulders 361a, 361b on housing sections 313, 314 (FIG. 13) prevent their separation except when snapped apart by force but the two sections can telescopically move towards each other for a purpose that will become clearer.

In this case, the four liquid take-up elements in the form of glass capillary tubes 330 are carried by a glass capillary amount 340 best seen in FIG. 10 to form a capillary tube sub-assembly 335. Mount 340 has four peripherally spaced identical segments that retain the glass capillary tubes in a rearwardly splayed fashion in front press fit notches 340a and rearward appropriately apertured integral holders 340b. The glass capillary mount is fixedly retained within an open neck portion 314c of housing cap section 314 so that, in this embodiment, the four tubes protrude from the front neck portion opening 315 of the housing to form a close spaced square array at their tips 330d.

Blotting paper carrier or cartridge 360 is generally similar to that of the second embodiment: a rounded square integral plate 361 with four angularly spaced tubular cup supports 362a. These supports define bores 362b lined with longitudinal ribs 363c that in turn define seats for disc-like liquid absorbent retention elements or pads 330a of one of the materials discussed earlier, or other suitable material. The ribs 362c are flared and aligned to receive the rear open ends of glass capillary tubes 330 when the support 360 is at its foremost position. Again in this case, retention elements or pads 330a may be blotting papers selected to absorb and retain blood samples.

The rib structure allows the pads 330a some adjustment along the bores to compensate for different alignments that cause the pads to be contacted by tubes 330 at different times. Other arrangements might include providing individual spring loading for cup supports 362a or crossbalancing them in pairs.

Blotting paper carrier or cartridge 360 is detachably retained, by opposed resiliently deflectable hooks 382, on a front circular pad 384 of a complex spring structure 380. Spring structure 380 is an integral moulded piece of the form depicted in FIG. 12. It has a rear end plate 386 located on a ledge defined by ribs 313*d* of housing section 313, and also has a box-like pedestal 387 that defines a central chamber 388 for retaining a hydrophilic silica gel desiccant capsule 365. This capsule is for absorbing moisture from the blood samples on blotting paper retention elements 330*a*, for drying the blood samples while they are in situ within the device and readying them for dried blood spot analysis. The interior of housing section 313 behind end plate 386 is a suitable chamber 385 for any desired control or recordal electronics, e.g for time and date stamping use of the device.

Spring structure 380 has three resilient elements to smoothly bias cartridge 360 into contact with capillary tubes 330 while also allowing for variations in the relative positions of the blotting papers and the inner ends of the capillary tubes. These features include a zig-zag central web structure 383 atop pedestal 387 integrally connecting the pedestal and pad 384, and substantially sinusoidal filament elements 389 at each side.

The device 310 is delivered in package 311, protected from contamination. It is prepared for use by removal from the package and placed in an upright position on dual purpose cover/base 400, retained by adhesive patch 402. This cover/base 400 engages an overhanging rim 313*a* of housing section 313 to extend about and protect the projecting ends of capillary tubes 330.

A sample of liquid such as blood is collected by removing the pen format device 310 from its base 400 and bringing its capillaries 330 into contact with the pin prick blood drop. Once the capillary tubes are filled, the pen is returned into position in base 400 and forced into the base by pushing down on the housing 312. The force of the plunge engages a locking feature 390 (FIG. 8) to lockingly engage housing 312 with the base 390, and telescopically moves housing segments 313, 314 together to bring the blotting papers of carrier 360 into firm resiliently supported contact with the inner open ends of the capillary tubes 330: the tubes are received into the bores 362*b* into engagement with the blotting paper pads 330*a*. The spring structure 380 provides adequate but gentle and transversely variable responsive bias to minimise risk of damage to the tubes or pads.

Once contact between tube and pad is made, the whole of the liquid in the tube is wicked into, i.e. flows into and is taken-up by the blotting paper pad, where it is safely retained for subsequent recovery and analysis.

Once thus lockingly reengaged in its cover/base, the device 310 cannot be reused and is typically irretrievable from the base at the blood collection site. It must be delivered to an analysis site where special tooling is employed to disengage locking feature 390 and allow retrieval of the cartridge 360 from within the housing. In a preferred configuration, the array of absorbent pads is dimensioned to be automatically receivable in one or more standard analytical instruments. In other arrangements, cartridge 360 may include holes to allow ejection of pads 330*a*, or may be configured to serve as a sample well in analytic processes; or may include electromechanical elements.

In a particular application of the invention, the capillary tubes may be designed to take up the target liquid by pure capillary action and to retain the liquid during subsequent movement or transport notwithstanding the effects of gravity. It is known that the height a liquid travels inside a capillary, using capillary force, is governed by a number of parameters including the interfacial tension between the surface of the capillary, the liquid involved, and the air, the density of the liquid, and the gravitational force. It can thereby be shown that, for a given volume of a liquid (such as blood) to be collected, there are dimensions of the capillary at which the capillary force is overcome by the gravitational force. For example, for a volume of 3 µL or 5 µL of blood the capillary volume will preserve capillary force, whereas for a larger volume such as 10 µL or 20 µL, there are specific capillary dimensions for which the capillary force is overcome by the gravitational force and others for which it is not.

A consequence of this observation is that a commonly sought sample micro-volume, e.g. in the range 10 to 30 µL can be collected using a device such as device 310 in which the capillary tubes contribute a portion of the desired liquid volume, e.g. portions of 3 µL or 5 µL, for which the capillary draw action is more predictable and controllable. Depending on the end application, the portions of the desired volume can be collected separately, or in an alternative embodiment, the blotting paper support 360 may be modified to collect all of the liquid portions on a single blotting paper, or the four portions in pairs on two blotting papers.

In this fashion, a multiple capillary sub-assembly may be a good pathway to collect accurate and precise larger volumes of liquid. For example, a unitary borosilicate glass capillary body might contain 10 bores of 3 µL each. The suction of blood within these capillaries can if desired occur via capillary action only, until the 10 bores are entirely filled, resulting in 30 µL of liquid collected. Indeed, use of the device in an upright orientation would be recommended. The employment of the 3 µL bores has a number of advantages: the device can be used at any inclination since capillary force is the sole suction mechanism, and if used upright there is no risk of air bubble formation while collecting liquid. There is no dislodgement of the liquid out of the capillary bores when the device is agitated.

More generally, it has been found that aspirating into one end of a capillary and dispensing at the other end to a contacting retention element such as a liquid absorbent paper is an especially effective method of achieving precision and accuracy in analysis of very small volumes of liquid. This is all the more so for liquids such as blood that have a high surface tension. Aspiration and dispensing from the same end, such as occurs with a pipette, risks lack of precision arising from minute liquid droplets retained at the outside of the orifice, and the contact with a wicking material removes this source of imprecision at the dispensing orifice.

In a further modification, any of the above described embodiments may include an in situ analysis element, e.g. a marker responsive strip or optical analyser, and a display for preceding a result of the analysis. For example, the liquid absorbent elements (30, 130, 230*a*; 330*a*) may be biosensor elements. An analysis of particular interest in this context is the protein marker haemoglobin A1c [HbA1c], now officially endorsed by the American Diabetes Association (ADA), International Diabetes Federation (IDF), and the European Association for the Study of Diabetes (EASD) to diagnose diabetes. Other examples include:

a modified porous substrate for the storage of biological samples such as described in US patent application 20140127669;

a modified porous substrate that enables separation of the plasma from whole blood such as described in US patent application 20150211967 A1;

the incorporation as part of the liquid absorbent element of an element for effecting blood plasma separation e.g. a Vivid plasma separation membrane (available from Pall Corporation);

the incorporation of a sensor to detect an analyte at the appropriate concentration in the collected volume of blood or plasma for monitoring diseases such as diabetes. Examples of appropriate sensors are:

a glucose sensor as described by Delaney et al, Anal. Chem. 2011, 83, 1300-1306 an immunological sensor for monitoring HbA1c using antibodies like those provided by AbD Serotec (http://www.abd-serotec.com/hba1c-hemaglobin-a1c-antibody.html)

a biosensor such as a modified optical fibre equipped with an appropriate microsphere for "Whispering Gallery Mode" detection as described by Francios et al, 2013, Optics Express 21, (19), 22566-22577.

It will be appreciated that the invention is applicable to the collection of precise and accurate very small (e.g. micro) volumes of a wide range of liquids for analysis. It is particularly useful for collecting blood samples, especially in the form of the third or fourth embodiment. It will be further appreciated that the device can be employed by an individual to collect blood samples from themselves, or more generally by relatively unskilled personnel to collect samples without any presence of skilled medical personnel. The liquid take-up element is maintained in a protected position prior to deployment and the sample is in turn retained in a manner that protects it from contamination between collection and recovery for analysis.

What is claimed is:

1. A pen format liquid collection device for collecting a sample of a liquid to be analysed, the collection device comprising:

an elongate generally tubular housing able to be held by hand and having an opening at one end;

at least one liquid take-up element comprising a capillary mounted in said housing, the at least one liquid take-up element positionable by hand manipulation of the housing to contact a volume of the liquid to be analysed, the capillary being dimensionally configured to define a predetermined liquid collection volume therein as determined by the internal dimensions of the capillary, such that the capillary is configured to thereby take-up by capillary action, the sample of said predetermined liquid collection volume, to fill the capillary and notwithstanding gravity, to retain the sample in any orientation of the capillary, and at least one retention element supported in said housing;

wherein the at least one capillary and the at least one retention element are arranged whereby they are relatively movable into contact;

whereupon said contact, the at least one retention element is adapted to in turn take-up the predetermined liquid collection volume of the sample and retain the predetermined liquid collection volume of the sample or a component thereof for in situ analysis or later recovery while protected within the housing;

wherein the capillary of the at least one liquid take-up element has a liquid collection volume in the range 1 to 10 μL.

2. The pen format liquid collection device as claimed in claim 1 wherein the at least one retention element is selected to take up the whole of the sample from the at least one capillary upon said contact.

3. The pen format liquid collection device according to claim 1 wherein the capillary is open at a first or distal end that in operation contacts said volume of liquid and at a second or proximate end that in operation contacts the at least one retention element.

4. The pen format liquid collection device according to claim 1 wherein the capillary of the at least one liquid take-up element has a liquid collection volume in the range 2 to 5 μL.

5. The pen format liquid collection device according to claim 1 wherein the at least one retention element is an absorbent body selected to absorb the whole of the sample from the at least one capillary when the two contact.

6. The pen format liquid collection device according to claim 1 wherein there are plural of said capillary within said housing.

7. The pen format liquid collection device according to claim 6 wherein there are plural said retention elements and each of the plural retention elements are contactable with a respective one of the capillaries.

8. A pen format liquid collection device, comprising:

an elongate generally tubular housing able to be held by hand and having an opening at one end;

a plurality of capillary liquid take-up elements in said housing comprising respective capillaries, which capillaries are, positionable, by hand manipulation of the housing, to contact a volume of liquid to thereby take-up a predetermined total volume of a sample of the liquid to be analysed, wherein each capillary is dimensionally configured to define a predetermined liquid collection volume therein as determined by the internal dimensions of the capillary such that each capillary is configured to take-up by capillary action, a respective sample portion being of said predetermined liquid collection volume, to fill the capillary, and notwithstanding gravity to retain the sample portion in any orientation thereof, and wherein the capillaries collectively take-up the predetermined total volume of the sample; and at least one retention element supported in said housing positionable to contact the capillaries, whereupon said contact, the at least one retention element is adapted to in turn take-up the predetermined total volume of the sample from the capillaries and retain the predetermined total volume of the sample or a component thereof for in situ analysis or later recovery while protected within the housing, wherein the capillaries each have a liquid collection volume in the range 1 to 10 μL.

9. The pen format liquid collection device according to claim 8 wherein the capillaries each have a liquid collection volume in the range 2 to 5 μL.

10. The pen format liquid collection device according to claim 8 wherein each capillary is open at a first or distal end that in operation contacts said volume of liquid and at a second or proximate end that in operation contacts the or each at least one retention element.

11. The pen format liquid collection device according to claim 8 wherein the at least one retention element is at least one absorbent body selected to absorb the whole of the sample from said capillaries on contact.

12. The pen format liquid collection device according to claim 8 wherein there are plural retention elements and each of the plural retention elements are contactable with a respective one of the capillaries.

13. The pen format liquid collection device according to claim 8 wherein there is a single retention element which is contactable with the plural liquid take-up elements.

14. The pen format liquid collection device according to claim 8 wherein the plural liquid take-up elements form a close spaced array at distal ends which are positioned or positionable to project at said opening.

15. The pen format liquid collection device according to claim 14 wherein the plural liquid take up elements are equi-angularly arranged about the housing in a splayed fashion.

16. The pen format liquid collection device according to claim 8 wherein a predetermined total volume is in the range of 10-30 µL and each capillary of the plurality of capillary liquid take-up elements comprise volume portions of 3 µL or 5 µL such that the predetermined total volume at least partially defines a number of the plurality of capillary liquid take-up elements.

17. The pen format liquid collection device according to claim 16 wherein each said capillary is designed to take up the sample by solely capillary action.

18. A pen format liquid collection device for collecting a sample of a liquid to be analysed, the collection device comprising:

an elongate generally tubular housing able to be held by hand and having an opening at one end;

at least one liquid take-up element comprising a capillary mounted in said housing, the at least one liquid take-up element positionable by hand manipulation of the housing to contact a volume of the liquid to be analysed, the capillary being dimensionally configured to define a predetermined liquid collection volume therein as determined by the internal dimensions of the capillary, such that the capillary is configured to thereby take-up by capillary action, the sample of said predetermined liquid collection volume, to fill the capillary and notwithstanding gravity, to retain the sample in any orientation of the capillary, and at least one retention element supported in said housing;

wherein the at least one capillary and the at least one retention element are arranged whereby they are relatively movable into contact;

whereupon said contact, the at least one retention element is adapted to in turn take-up the predetermined liquid collection volume of the sample and retain the predetermined liquid collection volume of the sample or a component thereof for in situ analysis or later recovery while protected within the housing;

wherein the at least one retention element is an absorbent body selected to absorb the whole of the sample from the at least one capillary upon said contact.

19. The pen format liquid collection device according to claim 18 wherein the at least one capillary and the at least one retention element are arranged whereby they are relatively movable into contact by hand action.

20. The pen format liquid collection device according to claim 18 wherein the capillary is open at a first or distal end that in operation contacts said volume of liquid and at a second or proximate end that in operation contacts the at least one retention element.

21. The pen format liquid collection device according to claim 18 wherein there are plural said capillaries within said housing and wherein there are plural said retention elements and each of the plural retention elements are contactable with a respective one of the capillaries.

22. A pen format liquid collection device, comprising:

an elongate generally tubular housing able to be held by hand and having an opening at one end;

a plurality of capillary liquid take-up elements in said housing comprising respective capillaries, which capillaries are, positionable, by hand manipulation of the housing, to contact a volume of liquid to thereby take-up a predetermined total volume of a sample of the liquid to be analysed, wherein each capillary is dimensionally configured to define a predetermined liquid collection volume therein as determined by the internal dimensions of the capillary such that each capillary is configured to take-up by capillary action, a respective sample portion being of said predetermined liquid collection volume, to fill the capillary, and notwithstanding gravity to retain the sample portion in any orientation thereof, and wherein the capillaries collectively take-up the predetermined total volume of the sample; and at least one retention element supported in said housing positionable to contact the capillaries, whereupon said contact, the at least one retention element is adapted to in turn take-up the predetermined total volume of the sample from the capillaries and retain the predetermined total volume of the sample or a component thereof for in situ analysis or later recovery while protected within the housing, wherein the at least one retention element is an absorbent body selected to absorb the whole of the sample from the at least one capillary upon said contact.

23. The pen format liquid collection device according to claim 22 wherein each capillary is open at a first or distal end that in operation contacts said volume of liquid and at a second or proximate end that in operation contacts the at least one retention element.

24. The pen format liquid collection device according to claim 22 wherein there are plural retention elements and each of the plural retention elements are contactable with a respective one of the capillaries to absorb the whole of the sample from the respective one capillary upon said contact.

25. The pen format liquid collection device according to claim 22 wherein there is a single retention element which is contactable with the plural liquid take-up elements to absorb the predetermined total volume of the sample upon said contact.

26. A pen format liquid collection device for collecting a sample of a liquid to be analysed, the collection device comprising:

an elongate generally tubular housing able to be held by hand and having an opening at one end;

at least one liquid take-up element comprising a capillary mounted in said housing, the at least one liquid take-up element positionable by hand manipulation of the housing to contact a volume of the liquid to be analysed, the capillary being dimensionally configured to define a predetermined liquid collection volume therein as determined by the internal dimensions of the capillary, such that the capillary is configured to thereby take-up by capillary action, the sample of said predetermined liquid collection volume, to fill the capillary and notwithstanding gravity, to retain the sample in any orientation of the capillary, and at least one retention element supported in said housing;

wherein the at least one capillary and the at least one retention element are arranged whereby they are relatively movable into contact;

whereupon said contact, the at least one retention element is adapted to in turn take-up the predetermined liquid collection volume of the sample and retain the predetermined liquid collection volume of the sample or a component thereof for in situ analysis or later recovery while protected within the housing;

wherein the housing includes a spring structure to bias the at least one retention element into said contact with the at least one capillary while allowing for transverse variation in the relative positions thereof.

27. The pen-format liquid collection device as claimed in claim 26 wherein the spring structure includes a zig-zag central web structure and substantially sinusoidal filament elements at each side thereof.

28. The pen format liquid collection device according to claim 26, wherein the at least one retention element is supported in a carrier or cartridge recoverable from the housing for subsequent analysis of the sample or component thereof, wherein the carrier is mounted on the spring structure.

29. The pen format liquid collection device according to claim 27 wherein the spring structure includes a central chamber for retaining a desiccant.

30. The pen format liquid collection device according to claim 29 wherein the zig-zag central web structure, the substantially sinusoidal filament elements and the central chamber of the spring structure are an integrally-moulded piece.

31. The pen format liquid collection device according to claim 26 wherein the housing is a two-part housing wherein the two parts are telescopically-slidable relative to one another, and wherein the at least one retention element and the at least one liquid take-up element are mounted to respective parts such that said contact is obtainable on relative sliding movement of the two parts by hand action.

32. The pen format liquid collection device according to claim 31 including a detachable cover about the end of the at least one liquid take-up element wherein the cover and the housing include interengagable formations for locking the cover to the housing by hand action.

33. The pen format liquid collection device according to claim 31 wherein the at least one retention element is supported by the spring structure provided on one of said parts.

34. A pen format liquid collection device, comprising:
an elongate generally tubular housing able to be held by hand and having an opening at one end;
a plurality of capillary liquid take-up elements in said housing comprising respective capillaries, which capillaries are, positionable, by hand manipulation of the housing, to contact a volume of liquid to thereby take-up a predetermined total volume of a sample of the liquid to be analysed, wherein each capillary is dimensionally configured to define a predetermined liquid collection volume therein as determined by the internal dimensions of the capillary such that each capillary is configured to take-up by capillary action, a respective sample portion being of said predetermined liquid collection volume, to fill the capillary, and notwithstanding gravity to retain the sample portion in any orientation thereof, and wherein the capillaries collectively take-up the predetermined total volume of the sample; and
at least one retention element supported in said housing positionable to contact the capillaries, whereupon said contact, the at least one retention element is adapted to in turn take-up the predetermined total volume of the sample from the capillaries and retain the predetermined total volume of the sample or a component thereof for in situ analysis or later recovery while protected within the housing,
wherein the housing includes a spring structure to bias the at least one retention element into said contact with the at least one capillary while allowing for transverse variation in the relative positions thereof.

35. The pen-format liquid collection device as claimed in claim 34 wherein the spring structure includes a zig-zag central web structure and substantially sinusoidal filament elements at each side thereof.

36. The pen format liquid collection device according to claim 34, wherein the at least one retention element is supported in a carrier or cartridge recoverable from the housing for subsequent analysis of the sample or component thereof, wherein the carrier is mounted on the spring structure.

37. The pen format liquid collection device according to claim 35 wherein the spring structure includes a central chamber for retaining a desiccant.

38. The pen format liquid collection device according to claim 37 wherein the zig-zag central web structure, the substantially sinusoidal filament elements and the central chamber of the spring structure are an integrally-moulded piece.

39. The pen format liquid collection device according to claim 34 wherein the housing is a two-part housing wherein the two parts are telescopically-slidable relative to one another, and wherein the at least one retention element and the at least one liquid take-up element are mounted to respective parts such that said contact is obtainable on relative sliding movement of the two parts by hand action.

40. The pen format liquid collection device according to claim 39 including a detachable cover about the end of the at least one liquid take-up element wherein the cover and the housing include interengagable formations for locking the cover to the housing by hand action.

41. The pen format liquid collection device according to claim 39 wherein the at least one retention element is supported by the spring structure provided on one of said parts.

* * * * *